(12) United States Patent
Müller et al.

(10) Patent No.: US 6,530,941 B1
(45) Date of Patent: Mar. 11, 2003

(54) DEVICE AND METHOD FOR FIXING, COMPRESSING OR SHAPING (PARTS) OF THE BODY

(76) Inventors: Christian Müller, Badstr. 28, 86830, Schwabmuenchen (DE); Michael Vogele, Badstr. 28, 86830, Schwabmuenchen (DE)

(*) Notice: Subject to any disclaimer, the term of this patent is extended or adjusted under 35 U.S.C. 154(b) by 0 days.

(21) Appl. No.: 09/463,149

(22) PCT Filed: Jul. 20, 1998

(86) PCT No.: PCT/EP98/04501
§ 371 (c)(1),
(2), (4) Date: May 10, 2000

(87) PCT Pub. No.: WO99/03398
PCT Pub. Date: Jan. 28, 1999

(30) Foreign Application Priority Data

Jul. 19, 1997 (DE) .......................... 197 31 040

(51) Int. Cl.[7] ................................................ A61B 17/00
(52) U.S. Cl. .......................................... 606/201; 601/24
(58) Field of Search ................. 606/201, 121; 128/870, 847, 845, 852; 601/6, 11, 24, 43, 44; 5/600, 601, 621, 624

(56) References Cited

U.S. PATENT DOCUMENTS

| | | | | |
|---|---|---|---|---|
| 2,563,501 A | * | 8/1951 | Sperling | |
| 3,286,693 A | * | 11/1966 | Clarke, Jr. et al. | |
| 3,642,006 A | * | 2/1972 | Wobbe | 606/121 |
| 3,783,863 A | * | 1/1974 | Kliever | |
| 3,859,982 A | * | 1/1975 | Dove | 601/24 |

FOREIGN PATENT DOCUMENTS

| | | | |
|---|---|---|---|
| EP | 0 728 446 A | * | 8/1996 |
| FR | 1278001 | * | 10/1961 |

* cited by examiner

Primary Examiner—David O. Reip
Assistant Examiner—Julian W. Woo
(74) Attorney, Agent, or Firm—Perkins Coie LLP (57) ABSTRACT

The invention relates to a device and method for fixing, compressing or shaping a body, or parts of the body, in particular the human body. The inventive device has a bearing surface (1) for the body, and at least one external element (2) which can be freely positioned on the bearing surface (1). The external element (2) and the bearing surface (1) together form a low-pressure chamber (6) which surrounds the body. The device also has at least one suction opening (3) which is connected to the low-pressure chamber (6).

43 Claims, 10 Drawing Sheets

DEVICE AND METHOD FOR FIXING, COMPRESSING OR SHAPING (PARTS) OF THE BODY

This patent application claims priority under 35 U.S.C. §365 from International Application No. PCT/EP98/04501, filed Jul. 20, 1998, which claims priority from German Application No. 197 31 040.0, filed Jul. 19, 1997, said application being incorporated herein by reference for all purposes.

This invention relates to an apparatus and a method for fixing bodies/body parts, especially of the human body or human body parts.

In many fields of human medicine or medical research and technology secure fixing of the patient or a person under investigation is necessary. This is of greatest importance especially in the field of diagnostic use (radiology), radiotherapy or in operative/surgical interventions (neurosurgery, ENT, etc.) but also during (acute or permanent) pre- or post-operative care of wounds/injuries. The requirements on accuracy and reproducibility, both in determining a stereotactical frame system in or on the human body and also in fixing the body itself, have been increased by the introduction of computer technology in diagnosis and therapy.

The following fixing methods are known as the state of the art:

a) fixing the body with adhesive tapes or cuffs: The body of the patient lies on a foam material pad. Tapes tensioned transversely over the body fix the patient on this pad. The following points are disadvantageous:
   indentation, pressure points, displacements and/or swelling of the skin can arise from the strong pull of the adhesive tapes;
   after removal of the retaining elements (adhesive tapes) it is hardly possible to effect repositioning in exactly the same position again, which is a disadvantage particularly in stereo-tactical operations and in radiotherapy;
   the body cannot be fixed adequately; movement in the sideways direction in particular (laterally) cannot be restricted or defined adequately.

b) fixing the body by screwing into the bone: The body of the patient is screwed to a metal frame at various places. The following are disadvantages:
   screwing to the bone is an invasive procedure and is thus only possible and justified for particular indications;
   the physical stress on the patient is substantial;
   the method can only be used for specific positions of the patient and impedes the operator;
   fixing of the soft parts (muscles, ligaments, connective tissue) is hardly possible at all.

c) fixing by formworks: The patient is placed on a kind of "air mattress", which is filled with foam material balls. By sucking the air out of this mattress, this becomes solid through the foam material balls lying against one another. The vacuum mattress is thus matched to the body in the first step and is sucked out in the second step. An impression of the body is obtained by this method. Disadvantages in this are:
   the "mattresses" usually employed do guarantee immobilisation but not fixing with uncooperative or anaesthetised patients adequate immobilisation is hardly possible at all;
   an inadequate impression of the patient often results, since the mattress can hardly bear exactly on all body parts;
   pressure points often result from formation of folds or too strong pressure, which can lead to pressure points and damage to tissues, especially with anaesthetised patients.

Other moulding materials, such as rails, thermoplastic material or plastics moulds, gypsum, etc. exhibit similar disadvantages. In addition, these methods involve substantial expenditure in money or time and are therefore only used for long-term applications.

The invention is therefore based on the object of providing an apparatus and a method for fixing/making moulds/compressing the human body or body parts, which avoids the cited disadvantages, is of simple structure and simple to use and kind to the patient to a high degree. The apparatus should moreover facilitate the exact application of calibration points (so-called markers) and optimal accessibility to operation regions.

This object is met by an apparatus according to the features described with reference to the present invention and the associated method.

In contrast to the apparatuses and procedures initially described, the fixing of the human body is effected in the proposed apparatus or method essentially by vacuum force. A blanket-like outer element is placed over a body support surface (flexible or rigid) with suction openings and is sucked at least substantially airtight on to the body support surface in its edge region projecting beyond the body (of the patient) A closed vacuum chamber thus results, so that the body is fixed relative to the support surface exactly and immovably in all directions.

The patient simply lies on the body support surface in the preferred arrangement and is "covered up" with the ox-like outer element. The patient or his body part(s) is/are now surrounded by this bag-like structure. Parts of the body (arms, legs, head, back) can emerge from the air or vacuum chamber through "peepholes" and thus remain unfixed, these openings being bounded by airtight arrangements, e.g. rubber bands or airtight cuffs. The air is now sucked out of the space between the body support surface and the outer element and the patient is fixed in the vacuum chamber thus resulting.

The described outer element or the body support surface is formed in the preferred embodiment from structurally reinforced, easily stretched plastics material or a metal foil and can accordingly adapt accurately to the anatomical structure of the body. By suitable choice of the material thickness and/or the level of the vacuum in the vacuum chamber an enhanced fixing or even compression of the body (of the patient) can be realised, so that the foil-like outer element lies like a second skin taut over the body (part).

By virtue of this fixing by means of vacuum it can be ensured that fixation which is always firm, exact and remaining constant is made possible, in particular after repeated use of the apparatus.

Vacuum pumps with adjustable degree of suction, hose connections and shut-off valves can be used as means for creating a vacuum. These devices can also be controlled/regulated in their vacuum action. In order to assist the vacuum action, shallow hollow spaces or vacuum channels can be formed by the creation of pores/channels on the outer element or the body support surface, which ensure uniform sucking out, for example by means of an air-bubble film with bumps known for protective packing. The previously described closed system can thereby also be operated as a semi-open system with constant sucking out of air, especially to facilitate the skin breathing during long operations.

A further method of achieving the described effect is to overlay and/or underlay between the outer element and the patient with a net/fleece/foam material or similarly structured material. Such materials ensure optimal flow of the air in all body regions, through the number of their air channels/pores in this application. Other media than air can also be used to create the vacuum. Possible "air-flow barriers" which are created by the suction or affect this are thus prevented. Pressure measuring devices serve to control a comparatively constant pressure on the body regions.

With a safety button the patient himself (e.g. in case of sickness or panic) or the operator (e.g. in case of complications during the intervention) can interrupt the vacuum (or even convert the vacuum briefly into a raised pressure) and thus release the body of the patient from the fixing very rapidly and without complication, since the outer element is then lifted "at a stroke" from the support surface.

The blanket-like outer element, preferably in the form of a heat protective aluminium foil known per se, can be packed sterilely as a disposable article but is also easy to clean and sterilise, so that the operating costs remain small, since all essential parts can be reused.

In addition to the pure fixation/compression/making moulds, auxiliary apparatuses (such as guide devices, optical apparatus, target devices, etc.) can be fitted by means of mechanical/pneumatic or magnetic anchorage, since the blanket-like outer element takes up hardly any additional space. Reproducible application with high accuracy is therefore possible through scaling or similar devices.

The body (part) can be so placed that practically any body region is completely accessible to the treating doctor or other treating person, especially for surgical interventions, while such an aluminum or plastics foil can be opened with a scalpel after application of the vacuum, without a pressure drop. An auxiliary fixing for additional securing of the patient constructed like the blanket-like outer element and thus capable of variable positioning is particularly advantageous. Above all in soft regions of the upper or lower abdomen or in the shoulder region, the fixing action can be enhanced by simple application of splint and support elements. The application of these splints additionally increases the repositioning accuracy. Likewise fixing of the patient, especially in the case of restless patients or of large applications of force from the outside, as in procedures with bones or cartilages, is ensured by this.

In addition this vacuum technique with at least one outer element lying on the body or the skin facilitates particularly uniform pressure distribution and thus relief of the patient. Injuries are practically ruled out, even with anaesthetised patients, who cannot give any indication of pain in case of pressure pain.

A particular advantage is also the application of passive or active calibration points on the outer element or the support surface, which determine reference points and reference planes in modern medicine in the practical application of imaging methods such as CT (computer tomography) or MRI (magnetic resonance imaging). The fixing apparatus thus allows calibration points to be applied to a part of the apparatus (primarily to the body support surface), which can be used as reference points for further measures, with or without fixing of the patient, such as calibration for preparations for operations for example.

If the objective is not only fixation but also reproducible positioning, additional prefabricated formwork, bands, vacuum mattresses can be used, which enhance the reproducibility. Since the body of (the patient) "wanders" during the sucking out into the same position, especially with concave support surfaces, a high accuracy of repositioning can be established. The resistance between the patient and the formwork or between the patient and the outer element or body support surface can be kept particularly small by slip films, so that assumption of the correct position is effected by shear forces, without high expenditure of force.

Cushioning underneath further increases the comfort. By variable vacuum regulation the cushioning action can be partially removed by increasing the vacuum and the fixation be enhanced and vice versa, A different vacuum can be applied for different body regions or it can be varied during the course of a fixation, for example in order to exert a massaging effect to increase the blood flow.

The outer element can either by closed pressure tight, as is the case with an aluminium foil, or have fine pores/channels, whereby the desired vacuum can be maintained correctly by a permanent "flow", The air flowing in can be regulated in heat and moisture content, in order to achieve a desired cooling/heating or drying/moistening of the fixed body. It is also possible as a supplement to or instead of the inflowing air to use other gases or fluids, which accelerate the healing process of wounds for example. It is thus also possible to create an artificial climate under the sucked on outer element and in the vacuum chamber thus formed.

The described fix can either be used for the whole body or equally for individual body parts only. Thus broken bones for example and complex fractures can be immobilised by means of the described vacuum fixation, instead of by gypsum bandages. In a preferred method, formwork or splints with the anatomy to be achieved are incorporated in the vacuum bandage. The applied vacuum causes homogenous application of the formwork to the body parts or apply the body pans to these structures. With open wounds or major cut injuries, which result in a lot of scar formation, the vacuum bandage causes the wound edges to lie against one another and thus allows smooth surfaced closure. Thus a skin seam r at the skin surface can be dispensed with in many cases.

A further application is homogenous application and pressing on of materials and fabrics on to the skin surface of the patient. The material or fabric in question is applied to the desired site. The outer element is then laid on as the vacuum dressing. If the air is now sucked out, the applied material is necessarily applied to the skin surface. Instead of direct application to the skid surface the outer element can also be applied on other kinds of fabric and structures.

Cut-outs in the outer element or in the body support surface, which close airtight on the patient through edge seals, allow direct, optimum access to the patient for the operator. This "operation window", especially in the outer element, can be provided with an anatomically shaped, structure-giving element, depending on the body region, for example with an edge-reinforced rubber band. The airtight closure is achieved either through the characteristic of the outer skin itself, for example an inner rubberising, or through sealing materials (adhesives, rubber strips, etc.), Preferred embodiments will be explained and described in more detail in the following with reference to the drawings, in which:

A preferred embodiment comprises a body support surface 1 made from a light material transparent to X-rays, to or from which further plate parts can be attached or removed in modular manner (ability to extend, reduce). Extruded, double web plastics plates of PMMA can be used as such plates for example, as known from ceiling claddings for example. These hollow chamber plates form at the same time a suction chamber 16 in their interior, shown at the right in FIG. 10, which is in communication with a plurality of suction opening 3. The body support surface 1 is thus light and transportable. It can be attached at its sides to stable suspension devices 4, for example screw fittings, to an operating table. The body support surface 1 can be adjusted and turned at these attachments in the horizontal and vertical direction relative to the operating table, a high degree of rigidity being ensured in each position.

A foil-like outer element 2 is placed on the body support surface 1 serving as a reference base. Airtight zip fasteners, sticking, clamping and plug-in connections 9 serve in particular to fix the outer element 2 at the surrounding edge region and can be operated simply and rapidly and make a firm and tight closure against the external air possible. It should be noted that, with suitable choice of material, especially a thin plastics or metal foil as the outer element 2, it is possible to dispense with such fixing at the edge region, since such an outer element 2 itself clings flat at the edge region of the body support surface 1 and thus effects a seal, especially with inner rubberisation or similar coating. The outer element 2 can however be made relative stable in form as a plastics part, like a lid or a convex shell, like the (concave) body support surface 1, only then being applied to the body of the patient (denoted P) when a vacuum is applied.

The outer element 2 is first laid loosely on the patient P in the manner of a bedspread or a cloth and pressed down or fixed at the outer edge region of the body support surface. Then the medium (in particular air) in the vacuum chamber 6 thus formed (cf. FIG. 3) is sucked out through suction openings 3. The foil preferably used as the outer element 2 is increasingly applied to the patient P by the suction. The vacuum in the vacuum chamber 6 can be controlled permanently through measuring probes, Access openings 5 with cuffs in the outer element 2 make it possible for body parts to emerge from the vacuum chamber 6, so that fixation/making a mould/compression is avoided. Thus the respiratory tract and ears (eardrum inflation) can be freed from the applied vacuum.

The vacuum chamber 6 can form a system closed relative to the surroundings in the simplest implementation. One-time evacuation and closure of the system, for example by means of the shut-off valve 21 shown in FIG. 10, allows the vacuum present in the vacuum chamber 6 to be maintained constant for a long time. A further possibility however, especially for long operations, to make the system "half open" by provision of pores or air channels 23. The desired vacuum in the vacuum chamber 6 can then be maintained by permanent suction (under "flow") . Likewise de introduction of suitable media (cooling fluid, medication nutrient solutions, etc.) is then possible. Also materials issuing from the body (blood, wound secretions, . . . ) can be sucked off in advantageous manner. A further application would be the suction of fatty tissue under the skin with post-operative maintenance of the vacuum as a pressure dressing.

Figure 1:
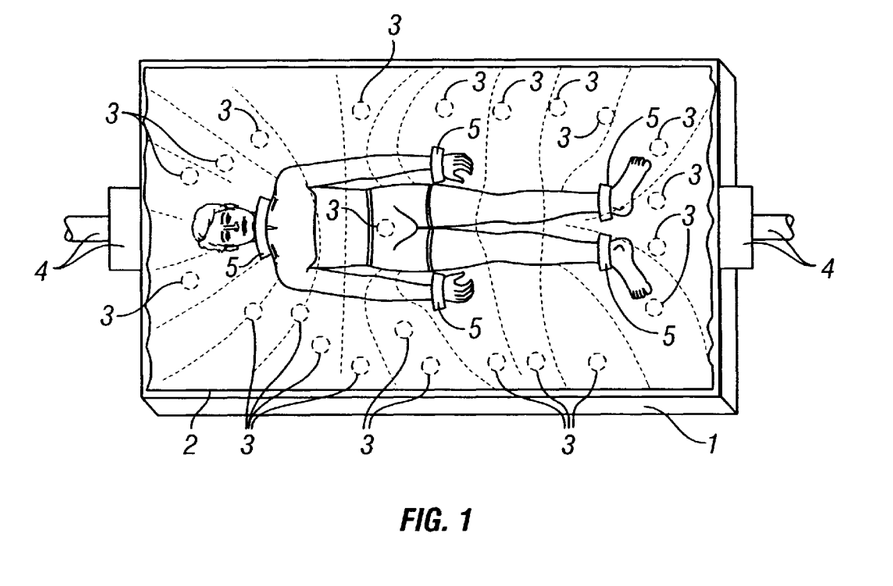
FIG. 1 shows an apparatus for fixing the body of a patient in a schematic plan view.
Figure 2:
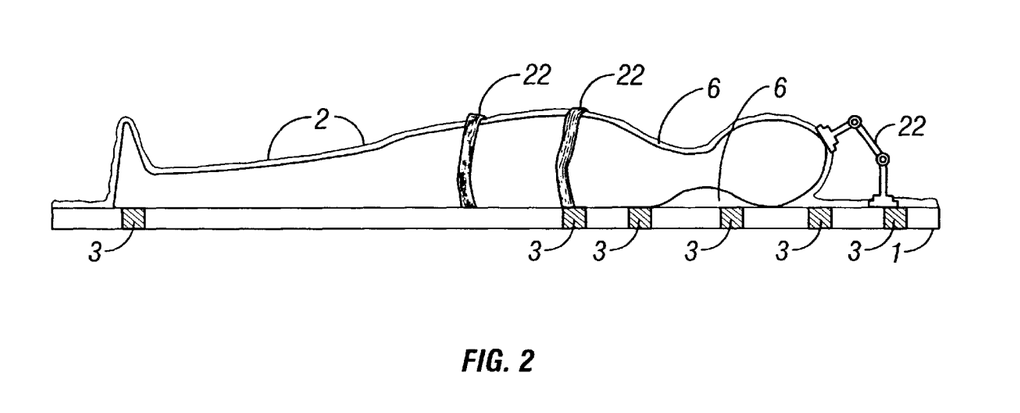
FIG. 2 shows the apparatus according to FIG. 1 in side view.
Figure 3:
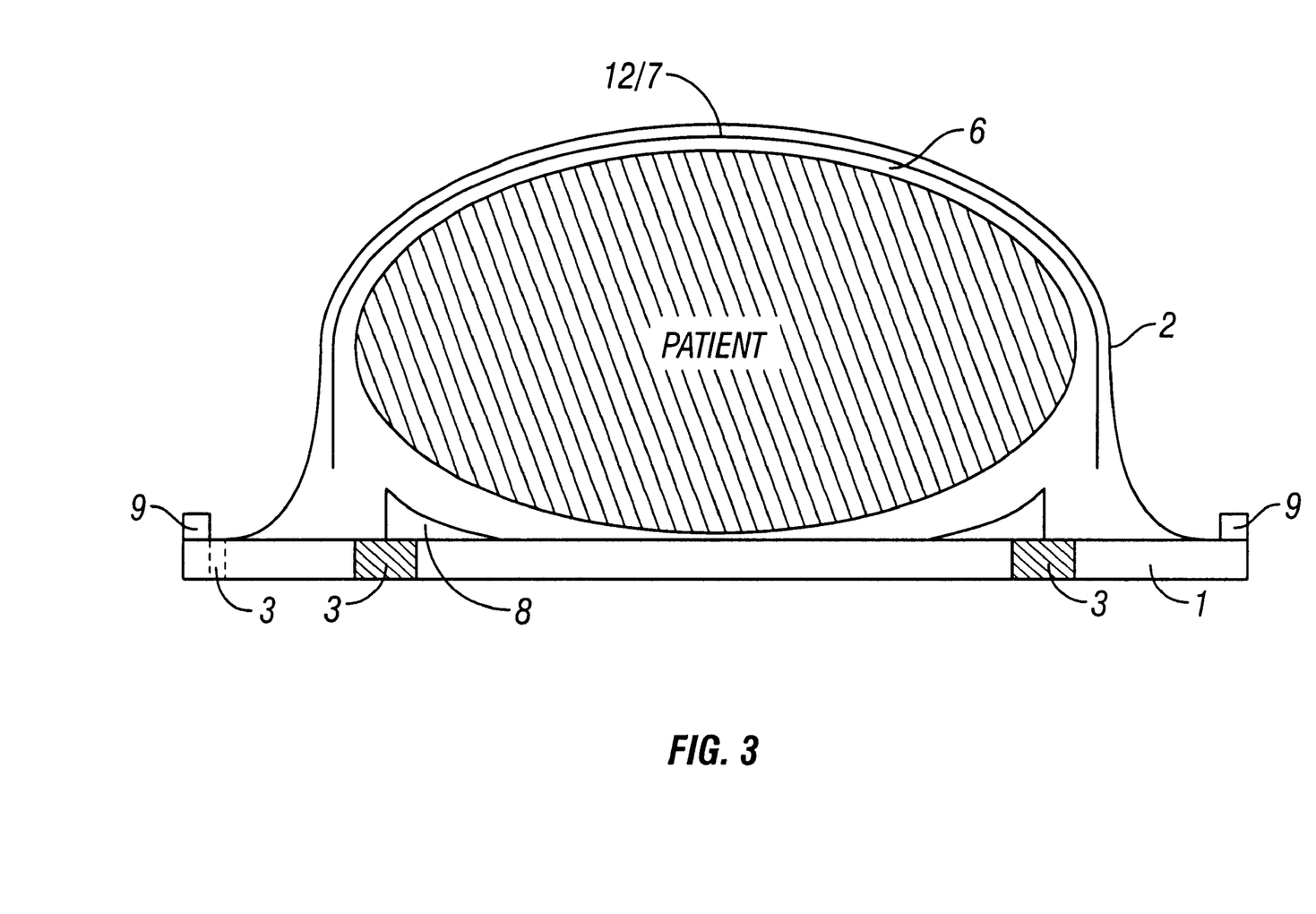
FIG. 3 shows the apparatus according to FIGS. 1 and 2 in cross-section.

As shown in FIG. 3 in particular, the patient P preferably lies on a support element 8, which is located between the patient P and the body support surface 1. This air-permeable patient support 8 is made relatively soft (e.g. fabric, fleece, pad, . . . ) and thus serves to enhance the comfort of lying, but can also be a solid, structure-imparting mould (e.g. a tray, concave cushion, etc.) and thus make reproducible positioning possible for multiple interventions. Similar insert elements 7, like the support element 8 can also be fitted between the outer element 2 and the patient P. The insert and support elements 7 and 8 can be freely movable and thus be adapted to the body of the patient P, or be fixed on the body support surface 1. They increase the accuracy of repositioning and make the support surface on the body support surface 1 larger.

Figure 7:
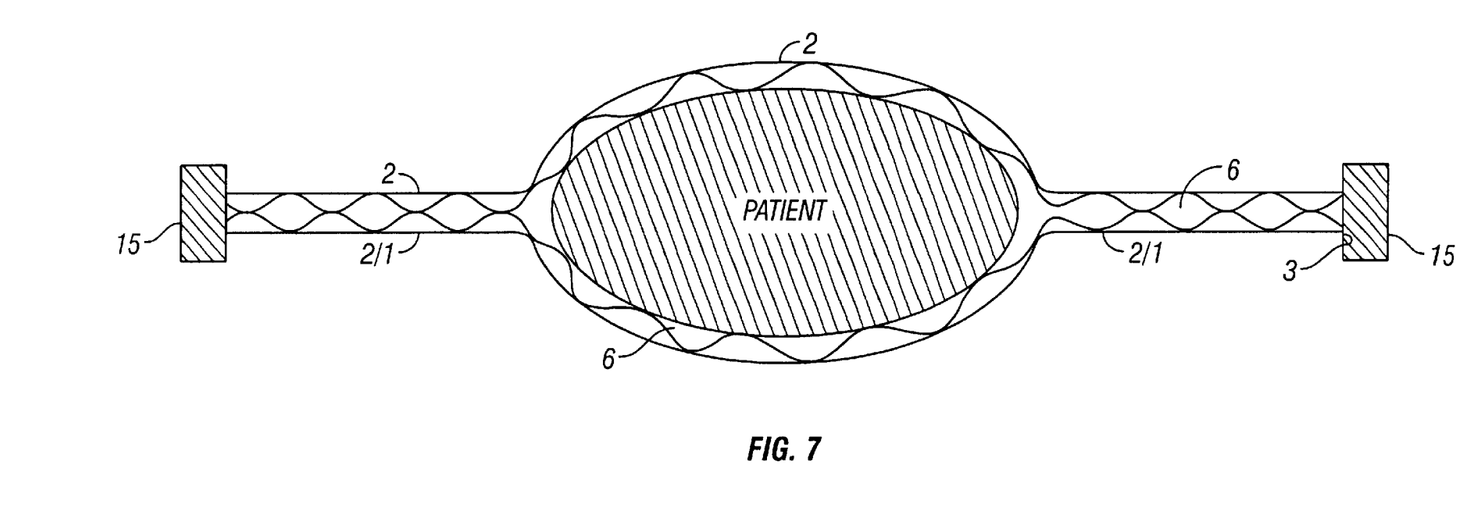
FIG. 7 is a sectional view of a two-sided, flexible patient covering or blanket with a fame suspension.
Figure 8:
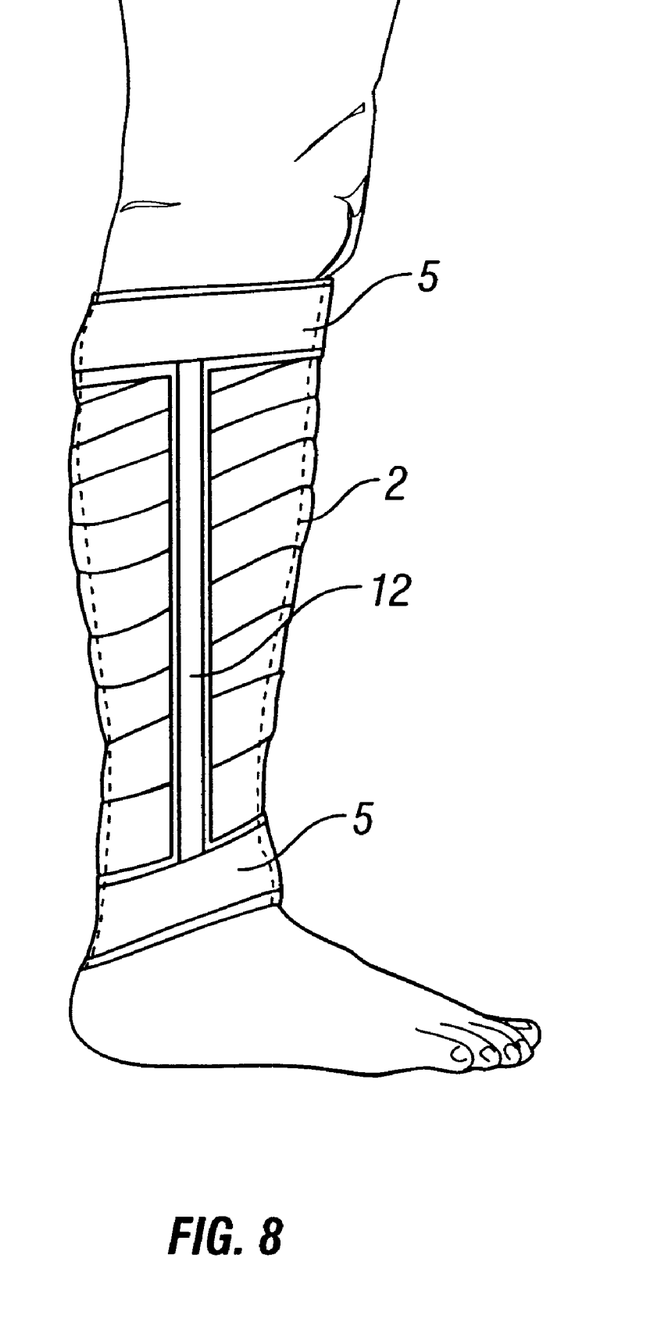
FIG. 8 shows a vacuum dressing with splints in side view.
Figure 9:
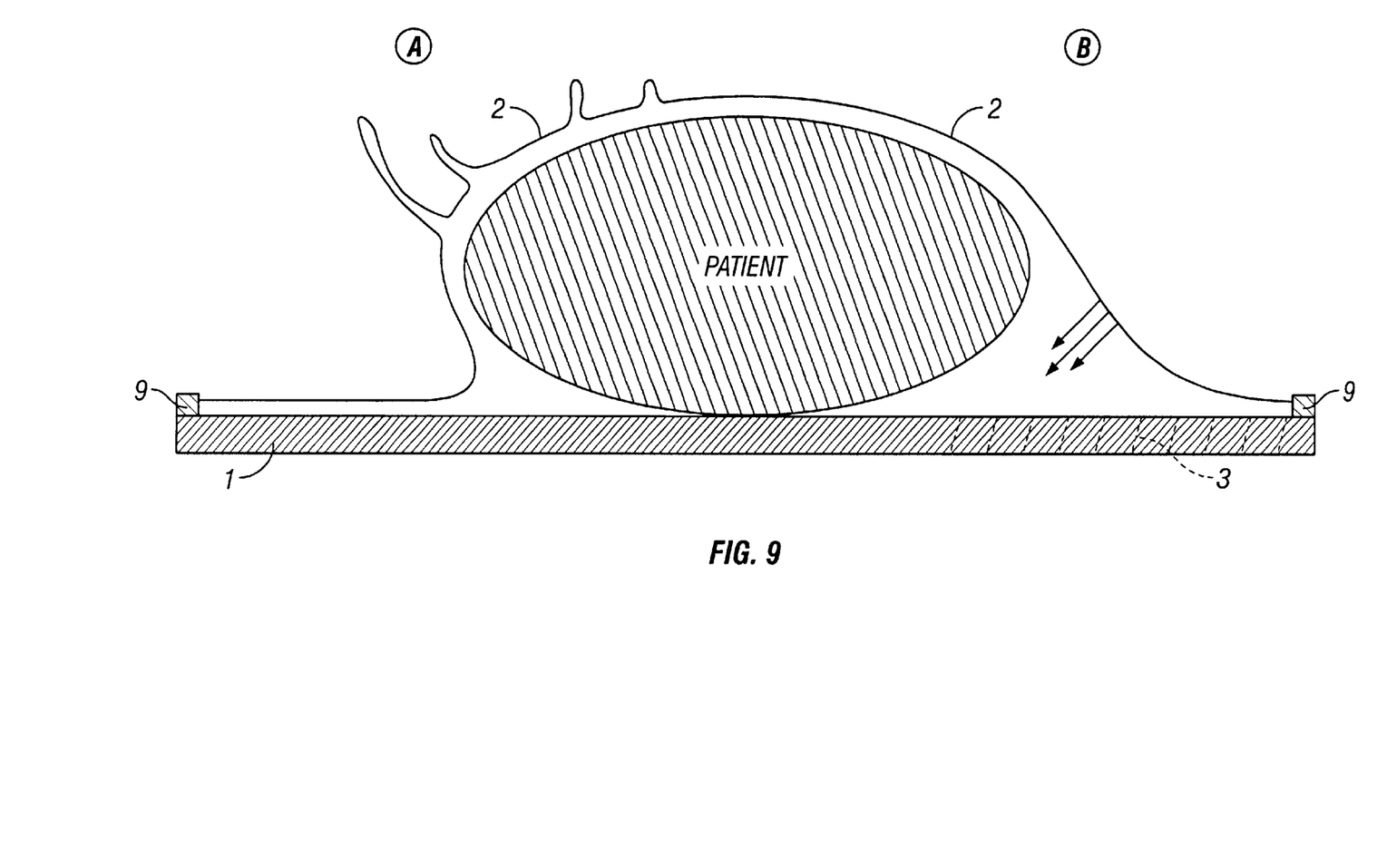
FIG. 9 is a comparative schematic drawing for illustrating a fixation/making a mould (A) and a compression (B) of a body, in cross-section.

An alternative to the flat body support surface 1 is offered by the use of a frame 15 shown in FIG. 7, in which two outer elements 2 are fixed, so that the body (or individual body parts) is completely enveloped by the outer skin, the patient therefore being suspended freely in fixed state in the frame 1S. The patient is completely surrounded by the outer elements 2 with this technology in the fixed state and, with an inextensible foil, practically the same pressure is exerted on all body parts in the fixed state. If on the other hand a rigid body support surface 1 or an outer element 2 which can only stretch moderately is used, the pressure on some body regions can be enhanced.

Figure 12:
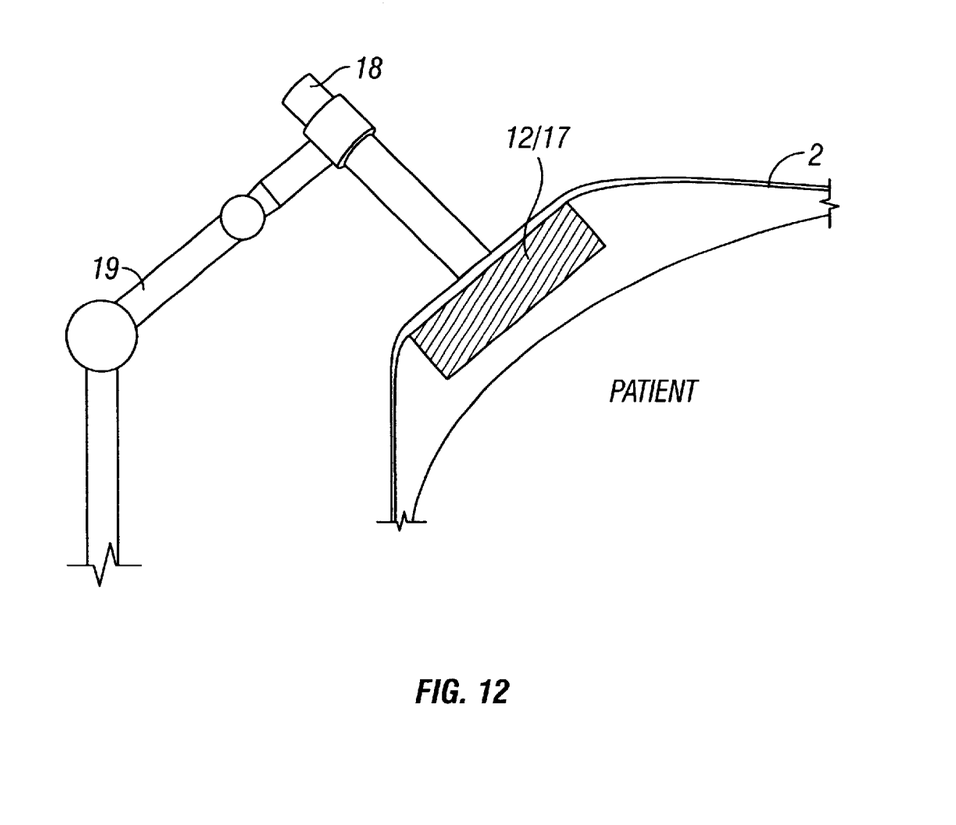
FIG. 12 is a schematic view of a guide device for formwork and splint elements.
Figure 13A:
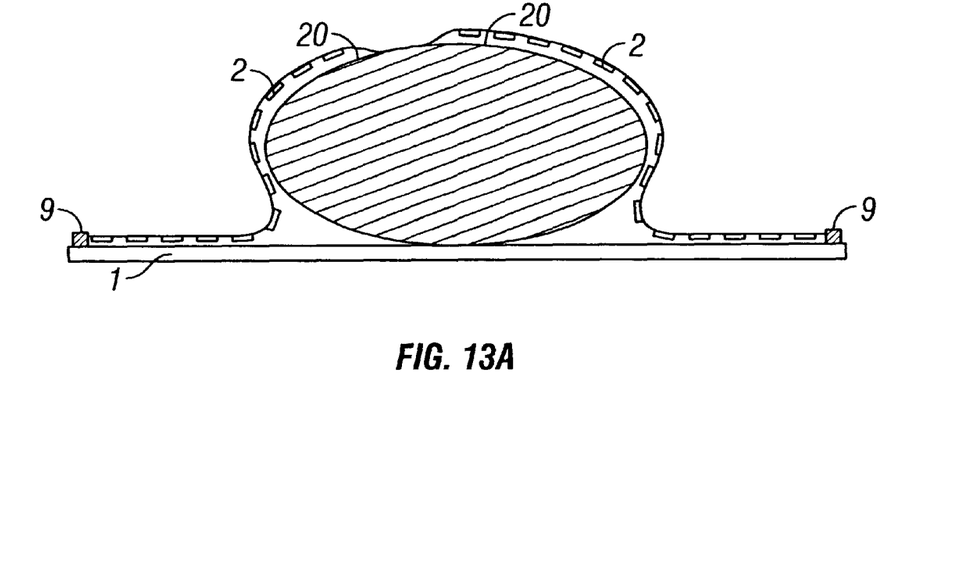
FIG. 13 shows an operation window in an outer element in cross-section and in plan view.
Figure 13B:
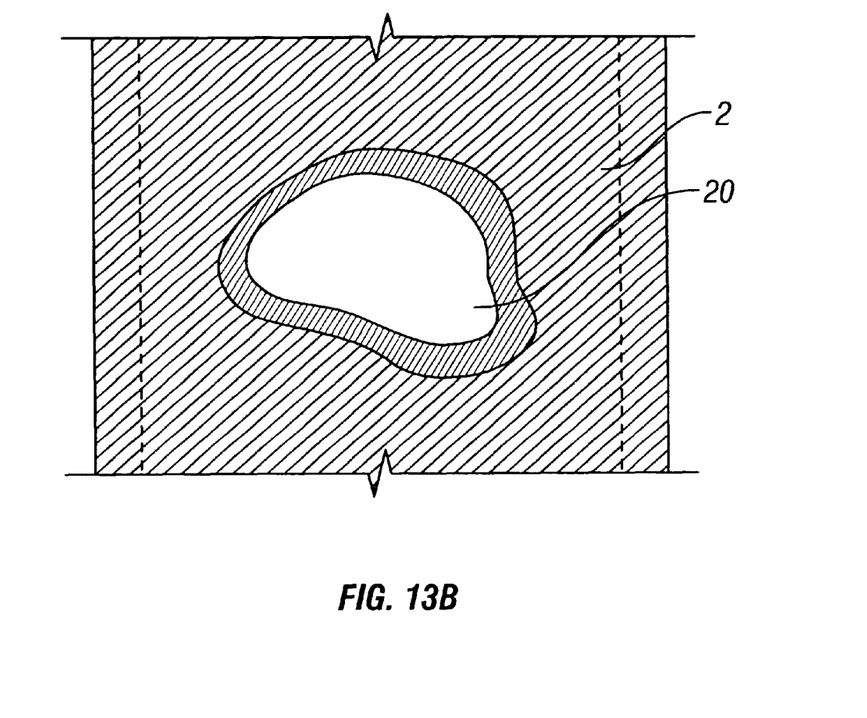

The body support surface 1 and the outer element 2 can also be subdivided by division into chambers. Independent pressure conditions can then be created in the individual chambers. In addition supplementary devices, such as freely positioned, stand-like support elements or retaining devices 18/19 (cf. also FIG. 12) can be fitted mechanically, magnetically or pneumatically on the body support surface 1.

Figure 4:
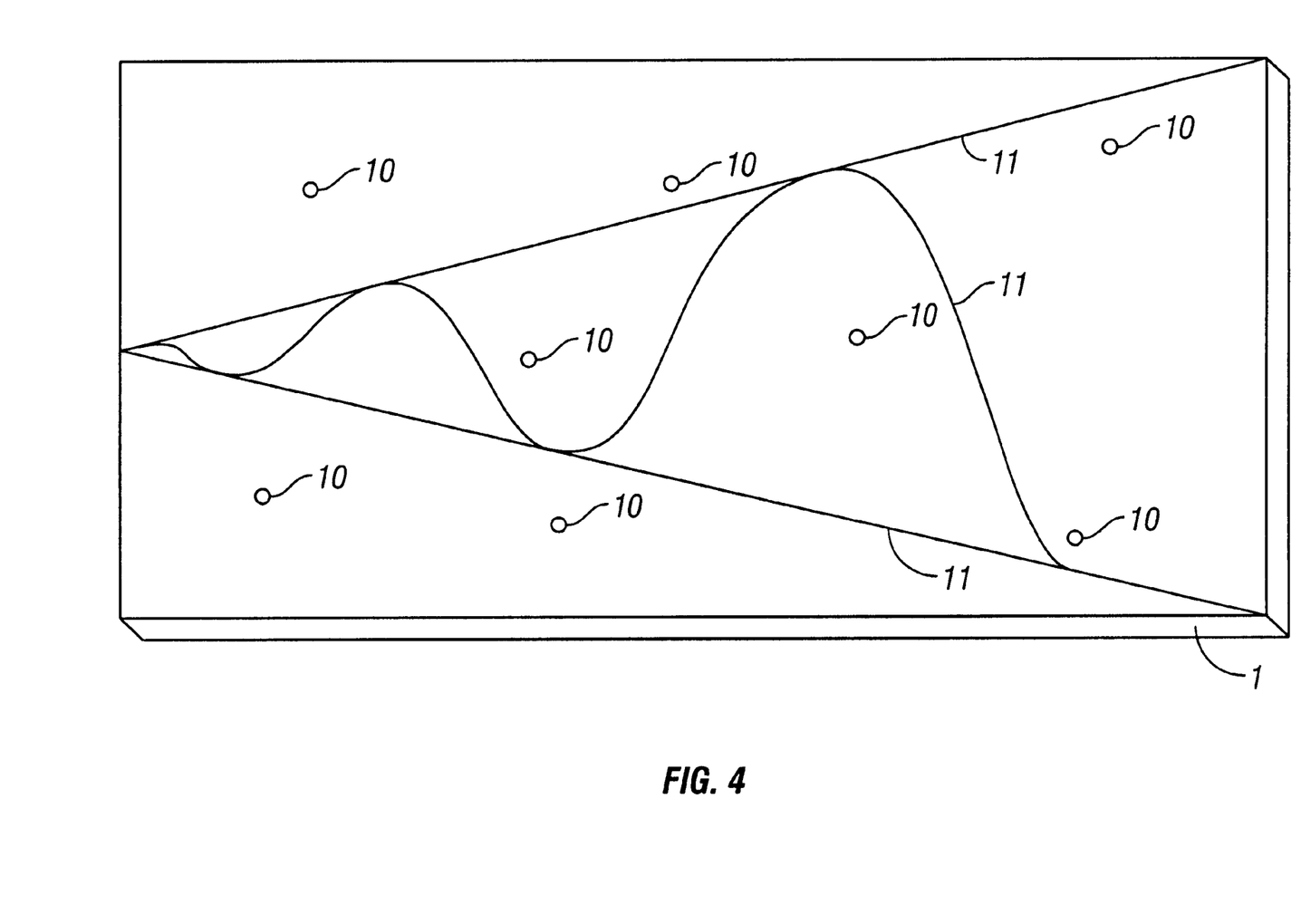
FIG. 4 shows a preferred application of calibration systems to the support surface, in plan view.
Figure 5:
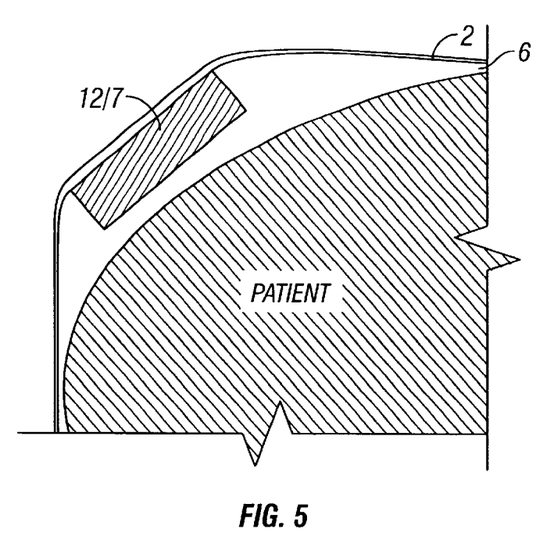
FIG. 5 shows a patient with a splint in cross-section.

With stereo-tactical operations reference points are further essential, where the previously described elements can also serve as holders for calibration points 10. The calibration points shown in FIG. 4 in the form of lead balls can serve as a simple reference system. However other sensor types can also be used, e.g. optical reflectors, radioactive or inductive emitters. Calibration lines 11 extending transversely over the body support surface 1 or the outer element 2 are also conceivable, allowing accurate conclusions as to the patient's position to be formed from their geometry. Such calibration systems or marker systems can thus be applied to the body support surface 1, the outer element 2 or also on the holding arms 19 or splints 12 or formwork 17 (cf. FIG. 12). The said splints 12 (e.g. strips or bands) can increase the fixing of the body region involved (e.g. with soft parts), especially in operations on regions which are hard to fix.

Figure 6:
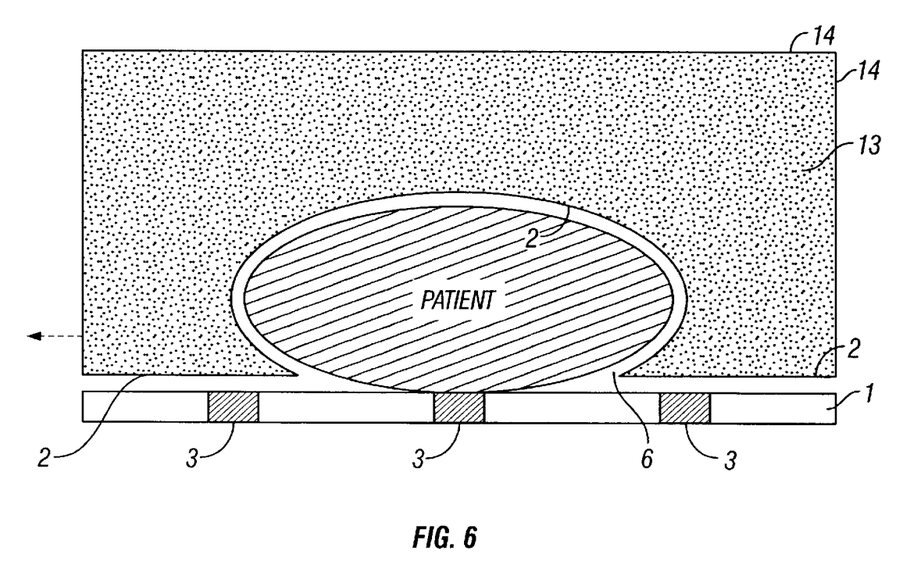
FIG. 6 is a sectional view of moulding by the vacuum method.

As shown in FIG. 6 moulding materials 13 can be filled in through a shaping container 14 (closed or open) fitted over the outer element 2, especially PU foam, gypsum or styro porous balls, which then can be fixed to make a body impression. Insert elements (strips, rubber mats) can be introduced in the moulding material 13. After hardening of the moulding material 13 individual insert elements can be pulled out and serve as vacuum channels within the outer element 2 individual to the patient thus formed for later repositioning.

Figure 10:
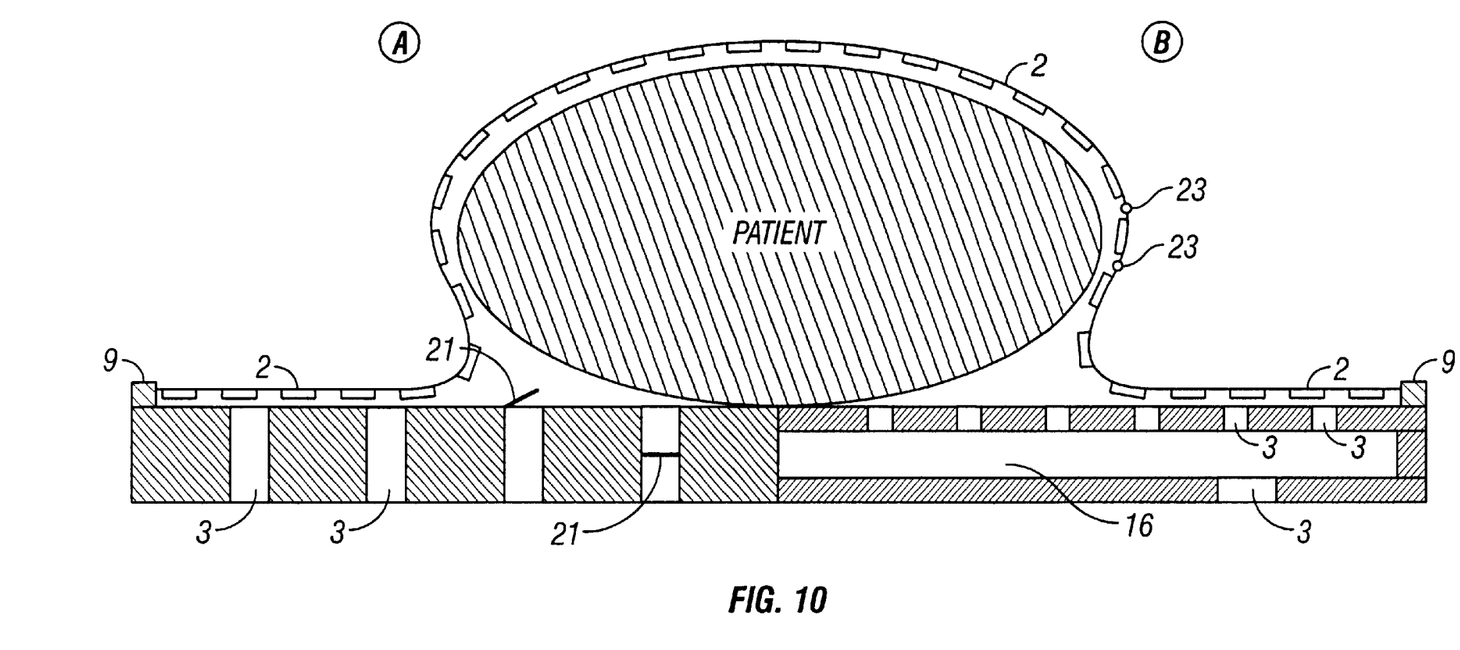
FIG. 10 is a schematic drawing for showing the suction with individual suction channels (A) and suction with a suction chamber (B), in cross-section.
Figure 11:
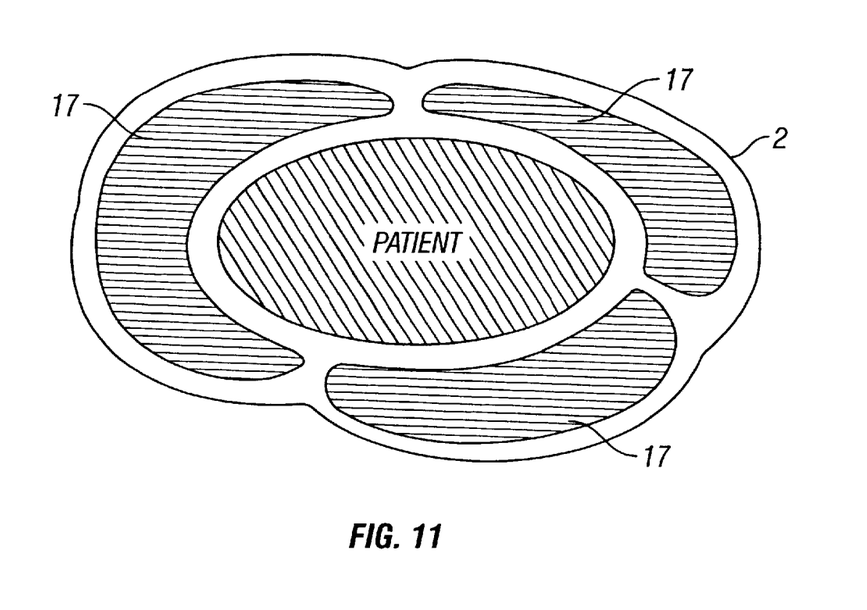
FIG. 11 shows a vacuum dressing with formwork in cross-section.

As shown in FIG. 10, the suction openings 3 can either lead directly into the vacuum chamber 6 or be connected to the vacuum chamber 6 through a suction chamber 16. In the latter arrangement a plurality of suction openings 3 connected to the suction chamber 16 can be operated uniformly with exactly the same vacuum. Such a suction chamber 16 or the described suction openings 3 (especially fine perforations in the upper wall of the body support surface 1) are present not necessarily only in the body support surface 1 but can also be fitted or integrated into the outer element 2.

The practical use of the proposed apparatus will be described as follows.

a) for (pure) fixation:
  for immobilisation during diagnostic procedures (CT, MRI);
  during operations, taking biopsies, irradiation, etc.;
  to immobilise patients, e.g. for psychiatrically ill patients ("vacuum straitjacket") or to avoid injury of somnolent/comatose patients;
  to immobilise body parts with (orthopaedic and surgical) injuries, with the advantage of simultaneous sucking away of wound secretions and/or compression of bleeding;

b) for compression:
  shock treatment with various forms of shock;
  care of amputations;
  suppression of bleeding in injuries to blood vessels/amputations;
  to simulate artificial pressure conditions (e.g. for training astronauts or divers);
  post-operative treatment (compression dressing, e.g. also for tattooing, application of cooling media);

c) for making moulds of body parts:
  exact application of moulding elements and masses (e.g. as PU foam);

d) for reproducible fixation:
  for repeated interventions, in which the same patient positioning is always necessary (especially all stereo-tactical uses: e.g. neuro-surgery, brachy-therapy, fractionated irradiation).

The advantages can be summarised as follows:

a) for fixation:
  uniform compression of the body (if desired);
  maximum visibility and freedom of movement for the operator;
  positioning of the body in variable positions during interventions;
  no displacement of the skin or shifts in position are possible;
  ability to introduce instruments, (e.g. an endoscope);

b) for reproducible fixation:
  definition of exact calibration points for stereo-tactical interventions (optical, radioactive or inductive sensors or emitters, etc.) in always the same relation to the body;
  small material outlay;

c) for making moulds:
  no fold formation in the foil outer element;
  highest accuracy through exact application by means of a vacuum;

d) general advantages:
  highest stability with small weight;
  suitability for diagnostic methods (CT, MRI);
  uniform pressure at all points or enhanced pressure at places with fitted splint elements;
  continuous pressure regulation is possible;
  space-saving construction;
  simple and time-saving handling through the vacuum application and therefore particularly kind to the patient and hygienic;
  high patient safety through control of the vacuum in the vacuum chambers and the pressure loading of the patient;
  in addition the possibility of immediate release and non-invasive fixing.

What is claimed is:

1. A low pressure chamber for surrounding at least a portion of a body comprising:
  a body support surface;
  at least one outer element, which can be positioned freely on the body support surface and forms with the body support surface a vacuum chamber surrounding the at least one portion of the body;
  at least one suction opening, which communicates with the vacuum chamber; and
  wherein the body support surface is formed elastically in a supporting direction.

2. A low pressure chamber as recited in claim 1, wherein the body support surface can be connected in an airtight manner to the outer element.

3. A low pressure chamber as recited in claim 1, wherein the outer element is of flexible, especially foil-like form.

4. A low pressure chamber as recited in claim 1, wherein the outer element is elastic in an applied direction and is inextensible in a transverse direction.

5. A low pressure chamber as recited in claim 1, wherein the body support surface is fittable to a table by means of a pivot suspension.

6. A low pressure chamber as recited in claim 1, wherein the outer element is so formed that it can be sucked onto an edge region of the body support surface.

7. A low pressure chamber as recited in claim 6, wherein the outer element is additionally fixable to the edge region of the body support surface at least one of mechanically, pneumatically and magnetically.

8. A low pressure chamber as recited in claim 6, further comprising fixings fitted to the edge region of the body support surface.

9. A low pressure chamber as recited in claim 1, wherein additional devices can be fitted on the body support surface at least one of mechanically, pneumatically and magnetically, said devices being capable of being repositioned.

10. A low pressure chamber as recited in claim 1, wherein the at least one suction opening is connected to at least one common suction chamber.

11. A low pressure chamber as recited in claim 10, wherein the at least one suction chamber is provided in at least one of the body support surface and the outer element.

12. A low pressure chamber as recited in claim 1, wherein the body support surface is divided into individual suction chambers.

13. A low pressure chamber as recited in claim 12 wherein the outer element is partially permeable to air by means of at least one of pores and flow channels.

14. A low pressure chamber as recited in claim 1, wherein the outer element is divided into individual vacuum chambers.

15. A low pressure chamber as recited in claim 12, wherein the outer element effects complete airtight closure.

16. A low pressure chamber as recited in claim 15, wherein at least one of the suction openings and suction chambers is closeable by means of a shut-off valve.

17. A low pressure chamber as recited in claim 1, wherein at least one of the body support surface and the outer element consists of individual modules joinable together.

18. A low pressure chamber as recited in claim 1, wherein the outer element is substantially similar in material and structure to the body support surface.

19. A low pressure chamber as recited in claim 1, wherein insert elements are fittable between a body and at least one of the outer element and the body support surface.

20. A low pressure chamber as recited in claim 19, wherein the insert elements are formed as at least one of splints and formwork in at least one of the outer element and the body support surface.

21. A low pressure chamber as recited in claim 1, further comprising preformed patient supports applied to at least one of the body support surface and the outer element.

22. A low pressure chamber as recited in claim 21, wherein the patient supports further comprise slip films.

23. A low pressure chamber as recited in claim 22, wherein the patient supports further comprise rubber mats.

24. A low pressure chamber as recited in claim 1, further comprising a moulding container for reception of a moulding material applied to the outer element.

25. A low pressure chamber as recited in claim 1, wherein the body support surface and the outer element further comprise at least one of a material permeable to X-rays and a non-ferromagnetic material.

26. A low pressure chamber as recited in claim 1, further comprising at least one of markings and peg bores on the body support surface for repositioning a patient.

27. A low pressure chamber as recited in claim 1, further comprising stretch-over devices on the body support surface.

28. A low pressure chamber as recited in claim 1, further comprising holding elements including at least one o magnetic and pneumatic holders, fitted to the body support surface for receiving medical apparatus comprising at least one of endoscopic apparatus, wound retractors, hand support surfaces and stereo-tactical navigational aids.

29. A low pressure chamber as recited in claim 1, further comprising fixation devices attachable to the body support surface.

30. A low pressure chamber as recited in claim 1, further comprising pressure measuring devices for controlling a pressure distribution in the vacuum chamber.

31. A low pressure chamber as recited in claim 1, further comprising a patient release mechanism operable to abruptly remove the vacuum in the vacuum chamber.

32. A low pressure chamber as recited in claim 1, wherein at least one of the outer element and the body support surface further comprises at least one access opening, the at least one access opening being sealed off around itself.

33. A low pressure chamber as recited in claim 1, further comprising operation openings which are sealed around and formed in at least one of the outer element and the body support surface.

34. A low pressure chamber as recited in claim 1, further comprising at least one adjustable calibration system formed in at least one of the body support surface and outer element for establishing a position of a plurality of reference points.

35. A low pressure chamber as recited in claim 1, wherein the outer element and the body support surface form a unit, the unit being formed in surrounding relationship to the at least one portion of the body like a bag.

36. A low pressure chamber as recited in claim 1, wherein the body support surface and the outer element are stretched in a frame suspension.

37. A low pressure chamber as recited in claim 1, wherein the body support surface and outer element further comprise an initially flexible material which hardens irreversibly, the material including a thermo-moulding material.

38. A low pressure chamber as recited in claim 1, wherein the at least one suction opening is formed as at least one individual suction channel.

39. A low pressure chamber as recited in claim 38, wherein the at least one individual suction channel is closeable by mean of a shut-off valve.

40. A low pressure chamber as recited in claim 1, wherein the outer element is substantially the same in material and structure to the body support surface.

41. A low pressure chamber as recited in claim 1, further comprising individually formed patient supports applied to at least one of the body support surface and the outer element.

42. A low pressure chamber as recited in claim 1, further comprising expansion devices disposed on the body support surface.

43. A low pressure chamber as recited in claim 1, further comprising compaction devices disposed on the body support surface.

* * * * *